United States Patent
Ewin et al.

(10) Patent No.: US 10,632,095 B2
(45) Date of Patent: Apr. 28, 2020

(54) LONG-ACTING KETOPROFEN COMPOSITIONS

(71) Applicant: Zoetis Services LLC, Florham Park, NJ (US)

(72) Inventors: Richard Andrew Ewin, Kalamazoo, MI (US); Steven X. Hu, Kalamazoo, MI (US); Susan M. Machkovech, Kalamazoo, MI (US); Barton H. Manning, Kalamazoo, MI (US); Stephen Lee Secreast, Kalamazoo, MI (US)

(73) Assignee: Zoetis Services LLC, Parsippany, NJ (US)

(*) Notice: Subject to any disclaimer, the term of this patent is extended or adjusted under 35 U.S.C. 154(b) by 0 days.

(21) Appl. No.: 15/102,020

(22) PCT Filed: Dec. 15, 2014

(86) PCT No.: PCT/US2014/070336
§ 371 (c)(1),
(2) Date: Jun. 6, 2016

(87) PCT Pub. No.: WO2015/095045
PCT Pub. Date: Jun. 25, 2015

(65) Prior Publication Data
US 2016/0303065 A1 Oct. 20, 2016

Related U.S. Application Data

(60) Provisional application No. 61/916,462, filed on Dec. 16, 2013.

(51) Int. Cl.
| | | |
|---|---|---|
| *A61K 31/216* | (2006.01) | |
| *A61K 47/14* | (2017.01) | |
| *A61K 47/44* | (2017.01) | |
| *A61K 9/00* | (2006.01) | |
| *A61K 47/10* | (2017.01) | |

(52) U.S. Cl.
CPC .......... *A61K 31/216* (2013.01); *A61K 9/0019* (2013.01); *A61K 9/0024* (2013.01); *A61K 47/10* (2013.01); *A61K 47/14* (2013.01); *A61K 47/44* (2013.01)

(58) Field of Classification Search
CPC ...... A61K 31/216; A61K 47/44; A61K 47/14; A61K 9/0019; A61K 9/0024; A61K 47/10
See application file for complete search history.

(56) References Cited

U.S. PATENT DOCUMENTS

| 4,614,741 A | 9/1986 | Dell et al. | |
|---|---|---|---|
| 2009/0062394 A1* | 3/2009 | Hartwig | A61K 9/7061 514/570 |
| 2010/0125060 A1 | 5/2010 | Razzak et al. | |
| 2012/0208887 A1 | 1/2012 | Douleau et al. | |

FOREIGN PATENT DOCUMENTS

| CN | 1709232 A | * 12/2005 |
|---|---|---|
| CN | 1709232 A | 12/2005 |
| CN | 102648897 A | 8/2012 |
| WO | 99/27906 A1 | 6/1999 |

OTHER PUBLICATIONS

CN1709232 (A); machine translation.*
Hoo-Kyun Choi, et al., "In vitro and in vivo study of poly(ethylene glycol) conjugated ketoprofen to extend the duration of action," International Journal of Pharmaceutics, vol. 341 (2007), pp. 50-57.
Pradeep Patil, et al. "Effect of Formulation Variables on Preparation and Evaluation of Gelled Self-emulsifying Drug Delivery System (SEDDS) of Ketoprofen," AAPS PharmSciTech 2004; 5 (3) Article 42 (http://www.aapspharmscitech.org), (2004) pp. 1-8.
Miho Shukuri, et al. "In Vivo Expression of Cyclooxygenase-1 in Activated Microglia and Macrophages During Neuroinflammation Visualized by PET with 11C-Ketoprofen Methyl Ester," The Journal of Nuclear Medicine, vol. 52, No. 7, Jul. 2011, pp. 1094-1101.

* cited by examiner

*Primary Examiner* — Sarah Pihonak
*Assistant Examiner* — Jason Deck
(74) *Attorney, Agent, or Firm* — Paul M. Misiak

(57) ABSTRACT

The invention describes a long-acting veterinary composition comprising at least one ketoprofen ester prodrug. The composition also comprises at least one veterinary acceptable triglyceride, and optionally, at least one preservative, and optionally, at least one additional veterinary acceptable excipient. The invention also describes a method of treating an animal for fever, pain, and/or inflammation by administering the long-acting composition comprising at least one ketoprofen ester prodrug to the animal in need thereof.

4 Claims, 7 Drawing Sheets

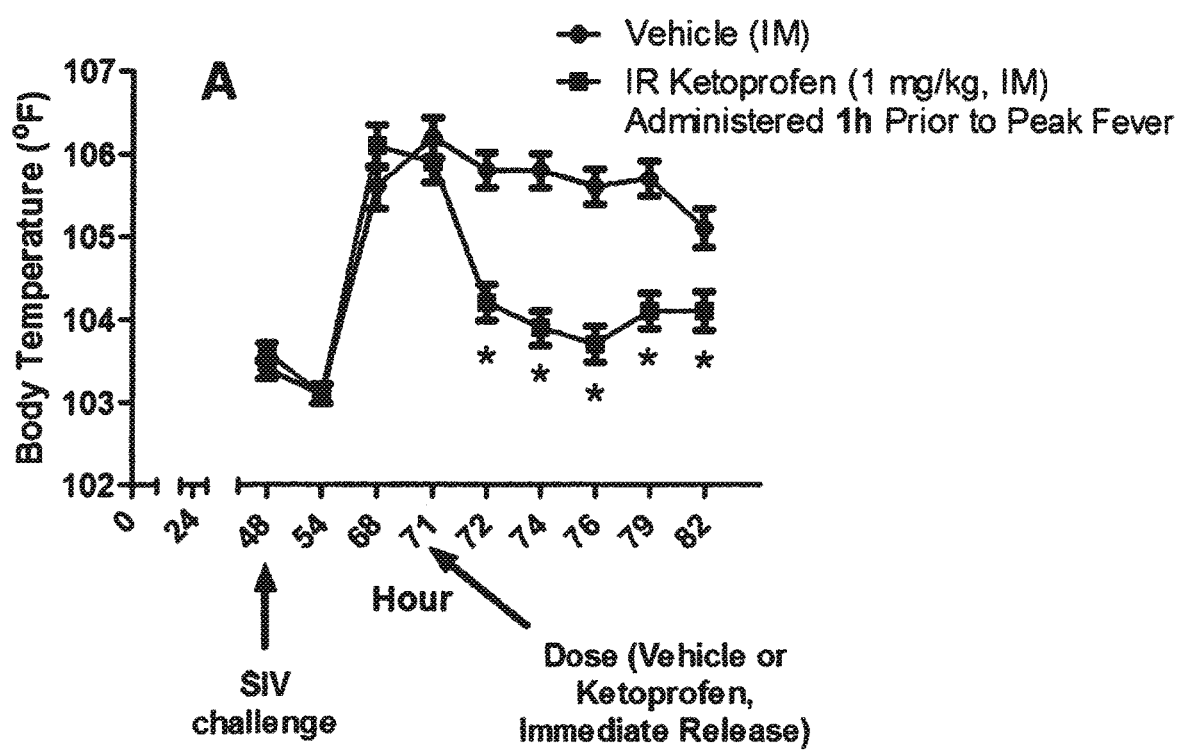
Figure 1A: Rectal Temperature Values in SIV Fever Model

Figure 1B: Rectal Temperature Values in SIV Fever Model
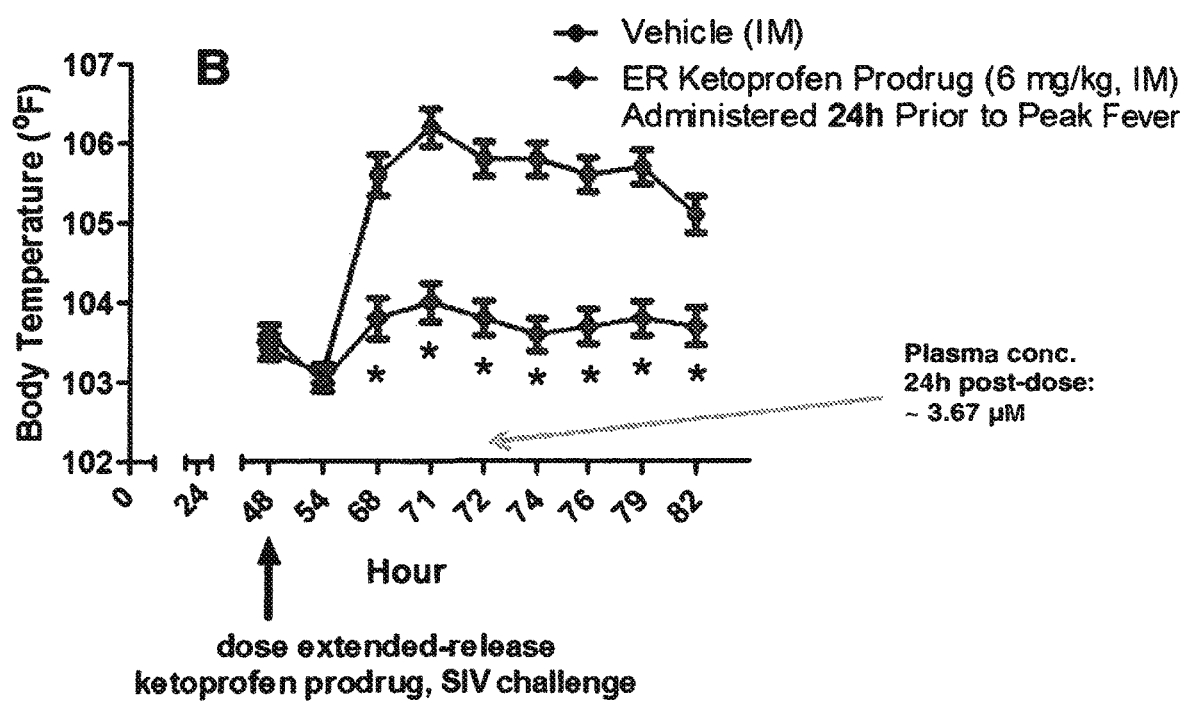

Figure 1C: Rectal Temperature Values in SIV Fever Model
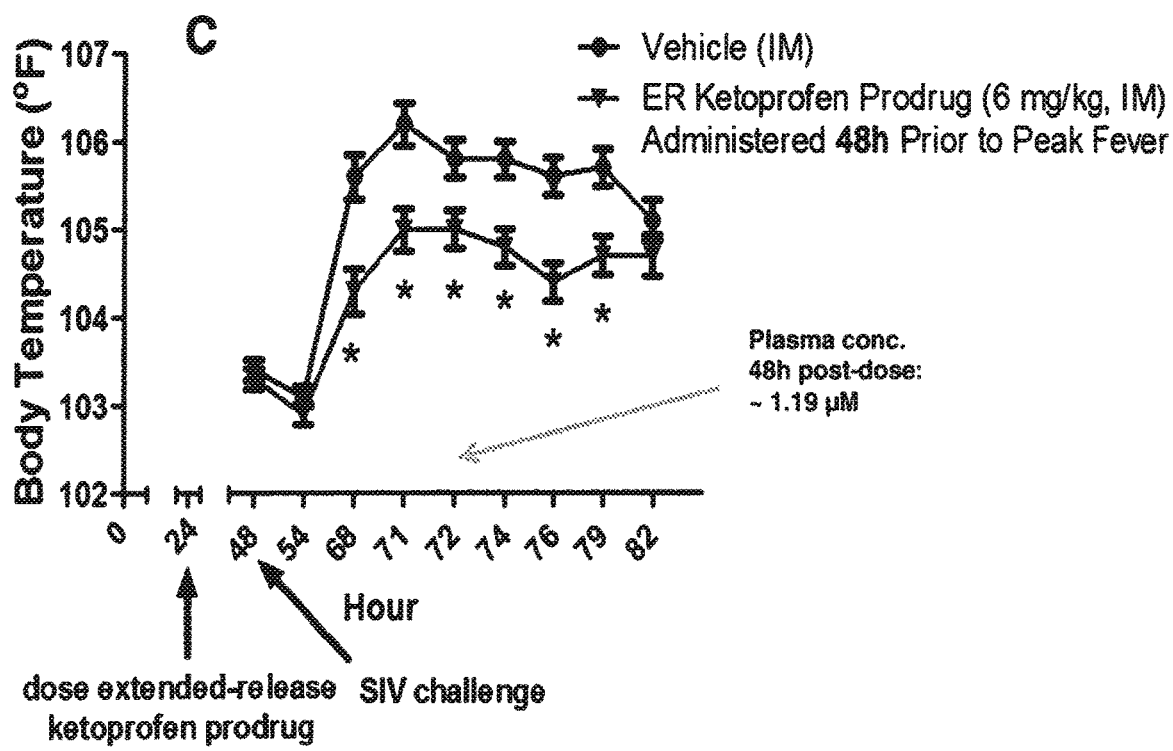

Figure 1D: Rectal Temperature Values in SIV Fever Model
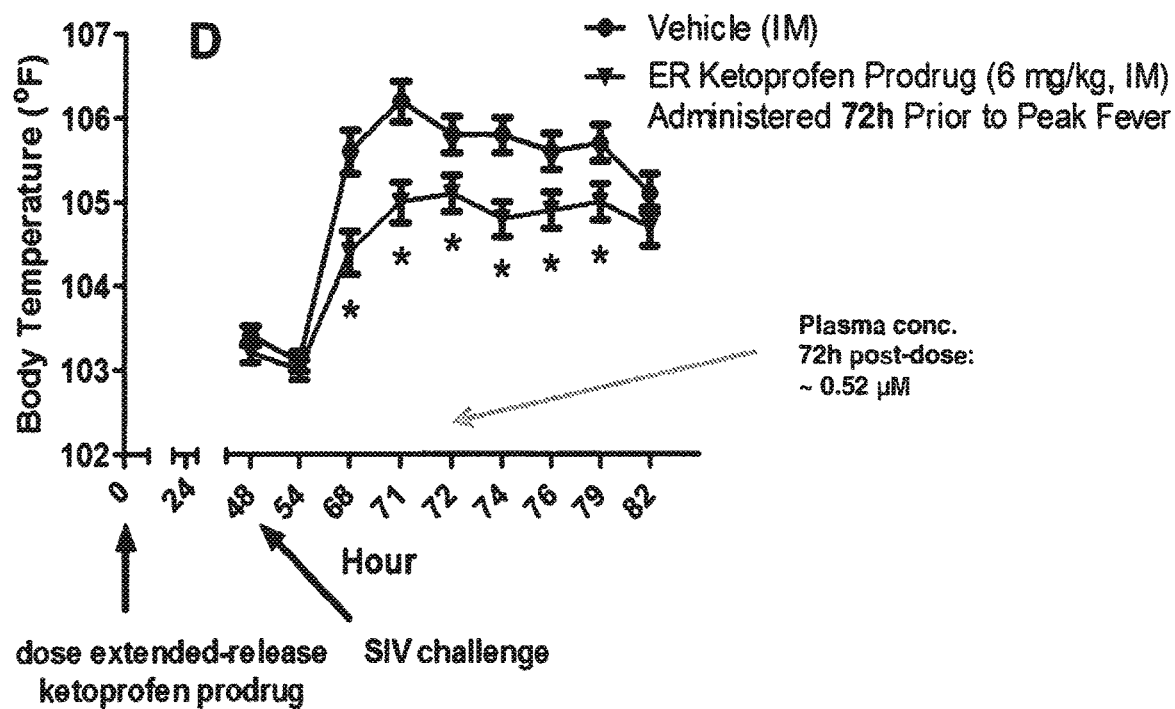

Figure 2. Rectal Temperatures in SIV Model – Onset of Efficacy
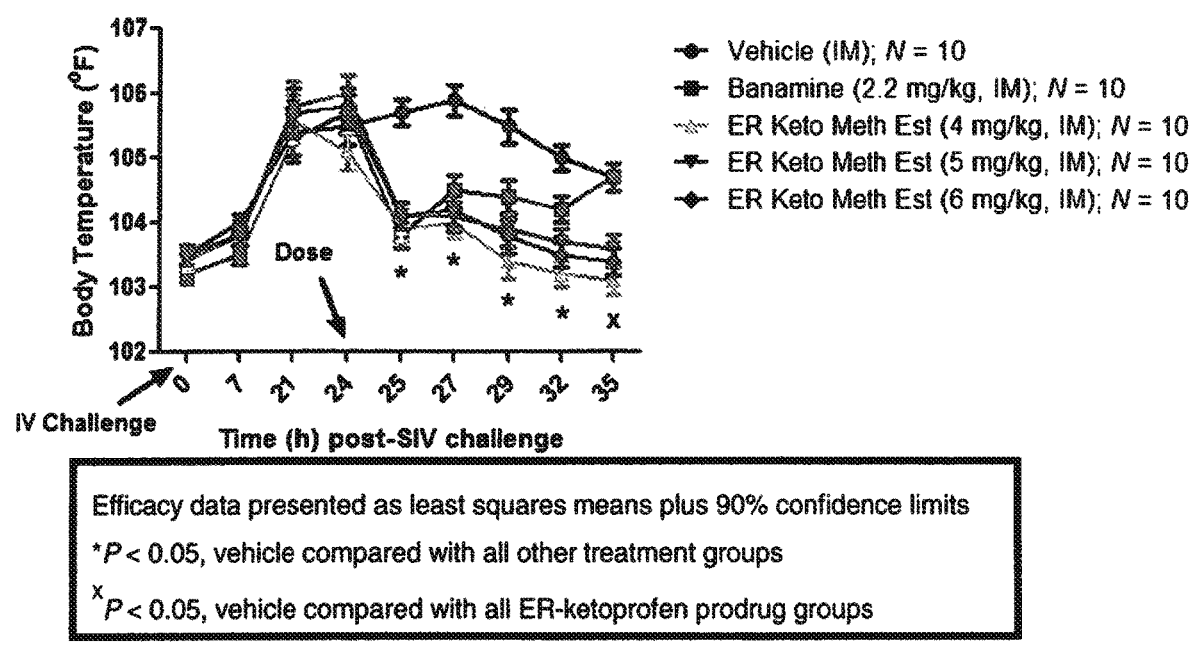

Figure 3A: Effects of extended-release ketoprofen methyl ester on lameness induced by intra-articular injection of LPS
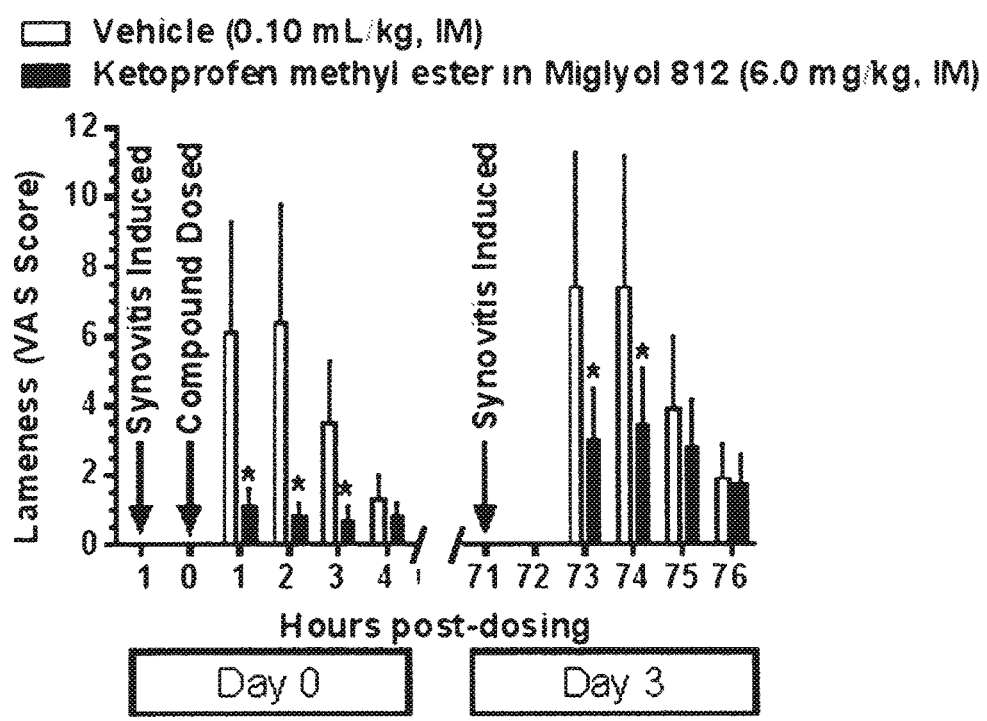

Figure 3B: Effects of extended-release ketoprofen methyl ester on lameness induced by intra-articular injection of LPS
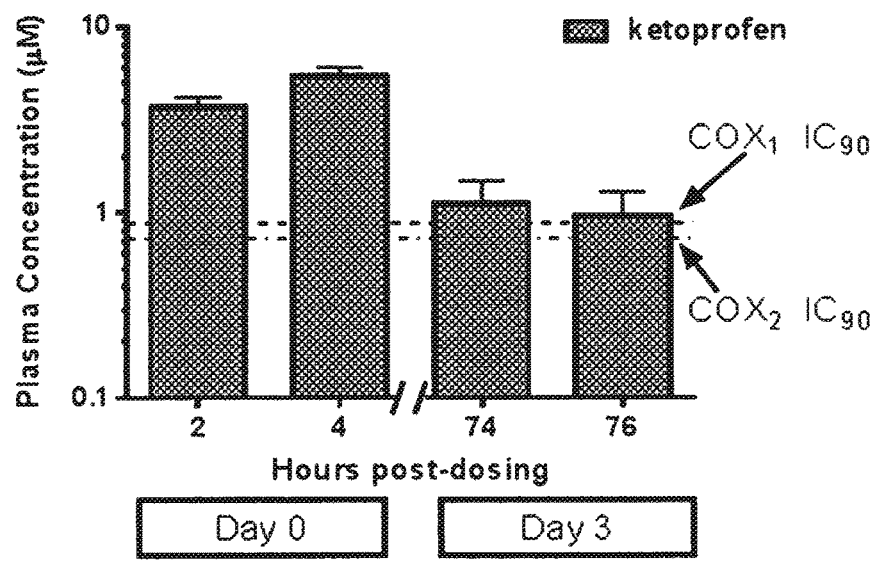

LONG-ACTING KETOPROFEN COMPOSITIONS

CROSS-REFERENCE TO RELATED APPLICATIONS

This application is the National Stage of International Application No. PCT/US2014/070336, filed Dec. 15, 2014, which application claims the benefit of U.S. Provisional Application No. 61/916,462, filed Dec. 16, 2013.

FIELD OF INVENTION

This invention relates to a novel long-acting composition comprising a ketoprofen ester prodrug, and at least one veterinary acceptable triglyceride, and optionally, a preservative and/or veterinary acceptable excipient. The invention also describes a method of treating an animal with fever, pain, and/or inflammation with said long-acting composition.

BACKGROUND OF THE INVENTION

The present invention relates to a novel long-acting composition comprising a ketoprofen ester prodrug and at least one veterinary acceptable triglyceride, and optionally, at least one preservative and/or at least one veterinary acceptable excipient. The invention also describes a method of treating an animal with fever, pain, and/or inflammation by administering said long-acting composition. Prodrugs of ketoprofen as well as ketoprofen are well known in the art. Similarly, there are many known topical, oral, and injectable compositions that can be used with ketoprofen and prodrugs thereof. The present invention provides an improved long-acting composition comprising at least one ketoprofen ester prodrug. In particular, the long-acting composition is an injectable composition.

The non-steroidal anti-inflammatory drugs (NSAIDS) inhibit the cyclooxygenase enzymes COX-1 and COX-2, thereby inhibiting the synthesis of prostaglandins which contribute to the generation of both fever and pain. Ketoprofen, 2-(3-benzoylphenyl)-propionic acid (racemate)

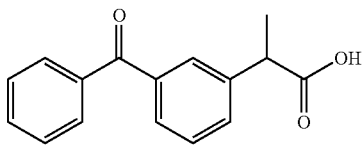 [SMILES: CC(C(=O)O)c1cccc(C(=O)c2ccccc2)c1]

is an NSAID that has long been recognized as being useful in the treatment of fever, pain, and/or inflammation (i.e., an antipyretic and analgesic agent). As an analgesic agent, ketoprofen is at least as effective as other available high potency NSAID compounds, such as indomethacin, meloxicam, flunixin meglumine, and phenylbutazone. As an antipyretic agent, ketoprofen is more potent than meloxicam.

Current NSAID treatments are designed for once-daily dosing and achieve varying degrees of success as measured by efficacy, including duration, and toxicity. Hence, there is a need for a stable and effective long-acting antipyretic and/or analgesic composition, particularly one that can provide from between 2 to 5 days of efficacy following a single injectable dose.

SUMMARY OF THE INVENTION

The present invention describes a long-acting ketoprofen composition for use in treating pain, inflammation and/or fever in animals. The long-acting composition comprises a) a ketoprofen ester prodrug, b) at least one veterinary acceptable triglyceride, and optionally c) at least one preservative, and optionally, d) at least one additional veterinary acceptable excipient. In another aspect of the invention, the long-acting composition comprises a) a ketoprofen ester prodrug and b) at least one veterinary acceptable triglyceride. In yet another aspect of the invention, the long-acting composition comprises a) a ketoprofen ester prodrug, b) at least one veterinary acceptable triglyceride, and c) at least one additional veterinary acceptable excipient. In yet another aspect of the invention, the long-acting composition comprises a) a ketoprofen ester prodrug, b) at least one veterinary acceptable triglyceride, and c) at least one preservative. In yet another aspect of the invention, the long-acting composition comprises a) a ketoprofen ester prodrug, b) at least one veterinary acceptable triglyceride, c) at least one preservative, and d) at least one additional veterinary acceptable excipient.

In another aspect of the invention, the ketoprofen ester prodrug is an alkyl-ester (for example, methyl, ethyl, propyl, isopropyl, and the like), benzyl ester, nicotinamide ester, a glycol ester (for example, polyethylene glycol ester, propylene glycol monoester and propylene glycol diester, and mixtures thereof). In another aspect of the invention, the ester is an alkyl-ester (for example, methyl, ethyl, propyl, isopropyl), and mixtures thereof. In another aspect of the invention, the ester is a methyl ester. In another aspect of the invention, the ester is an ethyl ester. In another aspect of the invention, the ester is a propyl ester. In another aspect of the invention, the ester is an isopropyl ester. In another aspect of the invention, the ester is a benzyl ester. In another aspect of the invention, the ester is a nicotinamide ester. In another aspect of the invention, the ester is a glycol ester (for example, polyethylene glycol ester, propylene glycol mono ester, propylene glycol diester, and mixtures thereof). In another aspect of the invention, the ester is a polyethylene glycol ester. In another aspect of the invention, the ester is a propylene glycol mono ester, propylene glycol diester, and mixtures thereof. In another aspect of the invention, the ester is a propylene glycol mono ester. In another aspect of the invention, the ester is a propylene glycol diester. In another aspect of the invention, the ester is a propylene glycol diastereomer.

In another aspect of the invention, the long-acting composition is a veterinary composition. In yet another aspect of the invention, the long-acting composition is an injectable veterinary composition. In yet another aspect of the invention, the long-acting veterinary injectable composition is an intra-muscular injectable composition. In yet another aspect of the invention, the long-acting veterinary injectable composition is a subcutaneous injectable composition.

In another aspect of the invention, the veterinary acceptable triglyceride (including triglyceride like) is selected from the group consisting of caprylic/capric triglyceride, propylene glycol dicaprylate/dicaprate (triglyceride like), caprylic/capric/linoleic triglyceride, glycerol triacetate (triacetin), castor oil, cotton seed oil; sesame oil, and mixtures thereof. In yet another aspect of the invention, the veterinary acceptable triglyceride is selected from the group consisting of caprylic/capric triglyceride, propylene glycol dicaprylate/dicaprate, glycerol triacetate, castor oil, cotton seed oil, and mixtures thereof. In yet another aspect of the invention, the veterinary acceptable triglyceride is selected from the group consisting of caprylic/capric triglyceride, glycerol triacetate, and castor oil, and mixtures thereof. In yet another aspect of the invention, the veterinary acceptable triglyceride is selected from the group consisting of caprylic/capric triglyceride and triacetin, and mixtures thereof. In yet another aspect of the invention, the veterinary acceptable triglyceride is selected from the group consisting of caprylic/capric triglyceride and castor oil, and mixtures thereof. In yet another aspect of the invention, the veterinary acceptable triglyceride is a caprylic/capric triglyceride. In still yet another aspect of the invention, the caprylic/capric triglyceride is Miglyol 812. In yet another aspect of the invention, the triglyceride is glycerol triacetate. In yet another aspect of the invention, the veterinary acceptable triglyceride is castor oil. In yet another aspect of the invention, the veterinary acceptable triglyceride is selected from propylene glycol dicaprylate/dicaprate, glycerol triacetate, castor oil, and mixtures thereof. In yet another aspect of the invention, the veterinary acceptable triglyceride is a mixture of two triglycerides, including propylene glycol dicaprylate/dicaprate and triacetin. In yet another aspect of the invention, the veterinary acceptable triglyceride is a mixture of two triglycerides, including propylene glycol dicaprylate/dicaprate and castor oil. In yet another aspect of the invention, the veterinary acceptable triglyceride is propylene glycol dicaprylate/dicaprate, particularly Miglyol 840.

In yet another aspect of the invention, the composition further comprises at least one preservative. In yet another aspect of the invention, the preservative is selected from the group consisting of butylated hydroxytoluene, butylated hydroxyanisole, benzyl alcohol, and mixtures thereof. In yet another aspect of the invention, the preservative is selected from the group consisting of butylated hydroxytoluene and butylated hydroxyanisole, and mixtures thereof. In yet another aspect of the invention, the preservative is butylated hydroxytoluene. In yet another aspect of the invention, the preservative is butylated hydroxyanisole. In yet another aspect of the invention, the preservative is benzyl alcohol.

In yet another aspect of the invention, the composition further comprises at least one veterinary acceptable excipient. In yet another aspect of the invention, the additional veterinary excipient is selected from the group consisting of tetraglycol, transcutol, Kolliphor HS15, polyethylene glycol, propylene glycol, pyrrolidones, ethanol, benzyl alcohol, glyceryl monostearate, glyceryl monooleate, ethyl oleate, isopropyl myristate, benzyl benzoate, and mixtures thereof.

In yet another aspect of the invention, is a method of treating an animal for fever, pain, and/or inflammation, comprising administering to said animal in need thereof a veterinary long-acting composition comprising a) a ketoprofen ester prodrug, b) at least one veterinary acceptable triglyceride, and optionally c) at least one preservative, and optionally d) at least one additional veterinary acceptable excipient. In yet another aspect of the invention, is a method of treating an animal for fever, pain, and/or inflammation, comprising administering to said animal in need thereof a veterinary long-acting composition comprising a) a ketoprofen ester prodrug and b) at least one veterinary acceptable triglyceride. In yet another aspect of the present invention, is a method of treating an animal for fever, pain, and/or inflammation, comprising administering to said animal in need thereof a veterinary long-acting composition comprising a) a ketoprofen ester prodrug, b) at least one veterinary acceptable triglyceride, and c) at least one preservative. In yet another aspect of the present invention, is a method of treating an animal for fever, pain, and/or inflammation, comprising administering to said animal in need thereof a veterinary long-acting composition comprising a) a ketoprofen ester prodrug, b) at least one veterinary acceptable triglyceride, and c) at least one additional veterinary acceptable excipient. In yet another aspect of the present invention, is a method of treating an animal for fever, pain, and/or inflammation, comprising administering to said animal in need thereof a veterinary long-acting composition comprising a) a ketoprofen ester prodrug, b) at least one veterinary acceptable triglyceride, c) at least one preservative, and d) at least one additional veterinary acceptable excipient.

In yet another aspect of the invention, is a method of treating an animal for fever, pain, and/or inflammation, comprising administering to said animal in need thereof a veterinary long-acting composition wherein the ketoprofen ester prodrug is selected from the group consisting of methyl ester, ethyl ester, benzyl ester, nicotinamide ester, polyethylene glycol ester, propylene glycol mono-ester, propylene glycol di-ester, propylene glycol mono- and di-ester, and propylene glycol diastereomers.

In another aspect of the invention is a method of treating pain in an animal by administering an effective amount of the veterinary long-acting composition of the present invention to an animal in need thereof. In another aspect of the invention is a method of treating fever in an animal by administering an effective amount of the veterinary long-acting composition of the present invention to an animal in need thereof. In another aspect of the invention is a method of treating inflammation in an animal by administering an effective amount of the veterinary long-acting composition of the present invention to an animal in need thereof.

In another aspect of the invention, the long-acting composition is administered by injection. In yet another aspect of the invention, the composition is an injectable composition. In yet another aspect of the invention, the injectable composition is an intramuscular (IM) injectable composition. In yet another aspect of the invention, the veterinary injectable composition is a subcutaneous injectable composition.

In another aspect of the invention, the amount of the ketoprofen prodrug is administered to an animal at a dose of about 0.5 to 12 mg/kg. In yet another aspect of the invention, the amount of the ketoprofen prodrug ranges from about 10 mg/mL to about 300 mg/mL.

In yet another aspect of the invention is the use of the long-acting composition of the present invention for the manufacture of a medicament for treating pain, fever, and/or inflammation in an animal in need thereof.

In another aspect of the invention is the use of the long-acting composition comprising a) a ketoprofen prodrug selected from the group consisting of Formula 1, Formula 2, Formula 3, Formula 4, Formula 5, Formula 6, and Formula 7, and mixtures thereof, b) at least one veterinary acceptable triglyceride, and optionally c) at least one preservative, and optionally d) at least one additional veterinary acceptable excipient for treating or preventing pain, fever, and/or inflammation in an animal in need thereof.

Definitions

For purposes of the present invention, as described and claimed herein, the following terms and phrases are defined as follows:

"About" when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

"Animal" as used herein, unless otherwise indicated, refers to an individual animal, and said individual animal is a mammal. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, and horse. Non-exclusive examples of livestock include: swine, goat, sheep, and cattle. Preferred livestock is cattle and swine. Preferred animal is swine, and yet a second preferred animal is cattle.

"Optionally", as used herein, unless otherwise indicated, refers to the voluntary inclusion of at least one preservative and/or at least one additional veterinary acceptable excipient; i.e., these additional ingredients are not required.

"Therapeutically effective amount", as used herein, unless otherwise indicated, refers to an amount of one of the ketoprofen prodrugs in a long-acting composition of the present invention that (i) treat or prevent the particular pyretic, inflammatory, and/or painful event, (ii) attenuates, ameliorates, or eliminates one or more symptoms of the particular pyretic, inflammatory, and/or painful event, or (iii) prevents or delays the onset of one or more symptoms of the particular pyretic, inflammatory, and/or painful event described herein. A dose range of about 0.5 to 12 mg/kg is contemplated to be a therapeutically effective amount.

"Treatment", "treating", and the like, as used herein, unless otherwise indicated, refers to reversing, alleviating, or inhibiting the pyretic, inflammatory, and/or painful event. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said pyretic, inflammatory, and/or painful event. Thus, treatment can refer to administration of the long-acting composition of the present invention to an animal that is not at the time of administration afflicted with the pyretic, inflammatory, and/or painful event, for example, as prophylactic treatment. Treating also encompasses preventing the recurrence of a pyretic, inflammatory, and/or painful event or of symptoms associated therewith.

"Veterinary acceptable" as used herein, unless otherwise indicated, indicates that the ketoprofen prodrug and long-acting composition must be compatible chemically and/or toxicologically with the other ingredients comprising the composition and/or the animal being treated therewith. The term is synonymous with pharmaceutically acceptable.

BRIEF DESCRIPTION OF THE DRAWINGS

FIG. 1A. Rectal Temperature Values in SIV Fever Model, Vehicle vs. IR Ketoprofen Administered 1 Hour Prior to Peak Fever
FIG. 1B. Rectal Temperature Values in SIV Fever Model, Vehicle vs. ER Ketoprofen Administered 24-Hours Prior to Peak Fever
FIG. 1C. Rectal Temperature Values in SIV Fever Model, Vehicle vs. ER Ketoprofen Administered 48-Hours Prior to Peak Fever
FIG. 1D. Rectal Temperature Values in SIV Fever Model, Vehicle vs. ER Ketoprofen Administered 72-Hours Prior to Peak Fever
FIG. 2. Rectal Temperatures in SIV Model - Onset of Efficacy
FIG. 3A. Effects of ER Ketoprofen Methyl Ester on Lameness Induced by Intra-Articular Injection of LPS
FIG. 3B. Effects of ER Ketoprofen Methyl Ester on Lameness Induced by Intra-Articular Injection of LPS

DETAILED DESCRIPTION

It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents.

The invention provides for a long-acting, stable, veterinary composition for the treatment of fever, pain, and/or inflammation in an animal in need thereof, which comprises administering an effective amount of a ketoprofen ester prodrug selected from the group consisting of a) methyl ester (Formula 1, methyl 2-(3-benzoylphenyl)propanoate), b) ethyl ester (Formula 2, ethyl 2-(3-benzoylphenyl)propanoate), c) nicotinamide ester (Formula 3, 2-(nicotinamido)ethyl 2-(3-benzoylphenyl)propanoate), d) benzyl ester (Formula 4, (benzyl 2-(3-benzoylphenyl)propanoate), e) propylene mono-ester (Formula 5, 2-hydroxypropyl 2-(3-benzoylphenyl)propanoate), f) propylene di-ester (Formula 6, propane-1,2-diyl bis(2-(3-benzoylphenyl)propanoate),g) mixture of Formula 5 and Formula 6, and h) polyethylene glycol ester (Formula 7). The propylene glycol esters of the instant invention, also include all diastereomers thereof.

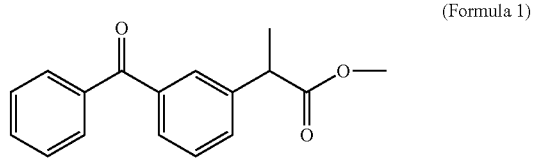

(Formula 1)

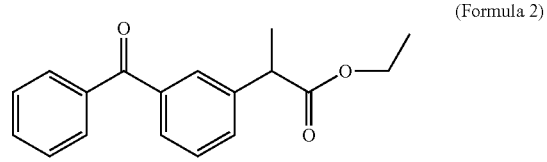

(Formula 2)

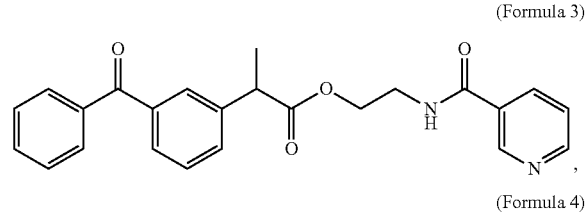

(Formula 3)

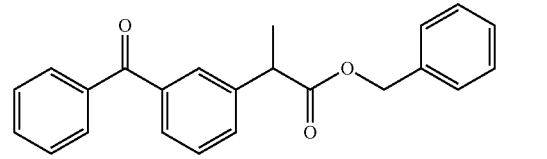

(Formula 4)

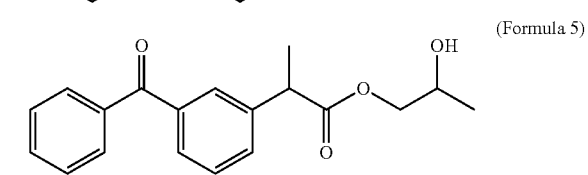

(Formula 5)

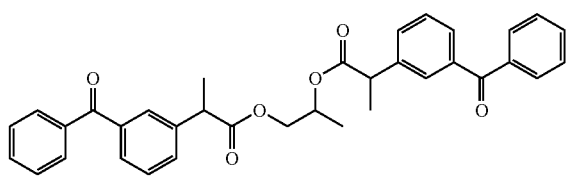

(Formula 6)

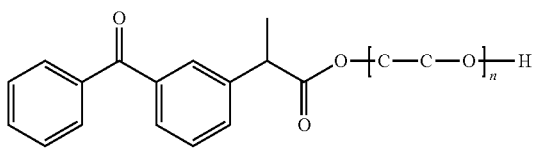

(Formula 7)

Following injection, the ketoprofen ester prodrug is gradually released from the formulation at the injection site. Once released into the systemic circulation (e.g., blood/plasma), the ester prodrug is hydrolyzed via liver enzymes. The parent (active) form of the drug, ketoprofen, is the predominant NSAID compound circulated that provides the established efficacy.

Ketoprofen can be prepared according to procedures described in U.S. Pat. No. 3,641,127. The alkyl-ester ketoprofen prodrugs can be prepared according to procedures described in the International Journal of Pharmaceutics, 43 (1988), pp. 101-110. Further, the methyl ester can be prepared using general esterification reactants as described by Liang, Yu-Feng, et. al., Highly Efficient C-H Hydroxylation of Carbonyl Compounds with Oxygen under Mild Conditions, Angewandte Chemie, International Edition, Volume 53, Issue 2, pages 548-552, 2014; Scheme 5. The nicotinamide ester ketoprofen prodrug can be prepared according to procedures described in the European Journal of Medicinal Chemistry, 39 (2004), pp. 715-727. The benzyl ester can be prepared by Fischer esterification which involves treating the carboxylic acid (ketoprofen) with an alcohol (for example, benzyl alcohol) in the presence of a dehydrating agent, for example, sulfuric acid, as described in Med Chem Res 21 (2012), pp. 3361-3368. The alkyl esters can also be prepared in this manner using an aliphatic alcohol. The glycol esters can be prepared in accordance with methods described in U.S. Pat. No. 4,560,785.

Ketoprofen exhibits potent anti-inflammatory, analgesic, and antipyretic actions that are associated with the inhibition of prostaglandin synthesis and antagonism of the effects of bradykinin. Ketoprofen non-selectively inhibits the activity of COX-1 and COX-2, which results in the blockade of prostaglandin production, particularly that of $PGE_2$, preventing the development of hyperalgesia. Ketoprofen has an $IC_{50}$ value of 4-8 nM in a non-selective human COX assay, being functionally 6-12 times more potent than other NSAIDs evaluated (e.g., naproxen or indomethacin). Kantor, T., Pharmacotherapy 6:93-103 (1986). Ketoprofen's $IC_{50}$ values against swine orthologs of the COX-1 and COX-2 enzymes are similar to human, in the 6-7 nM range, as described herein. By contrast, ketoprofen is less potent against bovine orthologs of the COX-1 and COX-2 enzymes, showing an $IC_{50}$ value of 30 nM against COX-1 and an $IC_{50}$ value of 220 nM against COX-2, as described herein. Ketoprofen also has functional bradykinin antagonist activity, its effects being 8-times greater than those seen with the classical NSAID, indomethacin. Julou, L., et al., Scand J Rheumatol Suppl 0:33-44 (1976). In addition to inhibiting cyclooxygenase, ketoprofen is believed to offer the additional anti-inflammatory benefit of inhibiting lipoxygenase.

Compositions, particularly veterinary compositions, more particularly, veterinary long-acting compositions, suitable for the delivery of at least one of the ketoprofen prodrugs of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

In the present invention, the veterinary acceptable triglyceride further encompasses the mono- and di-glycerides. Further, triglyceride encompasses the naturally-derived and semi-synthetic/synthetic oils, for example castor oil, cottonseed oil, sesame oil, linseed oil, safflower oil, peanut oil, soybean oil, coconut oil, olive oil, corn oil, almond oil, poppyseed oil, sunflower oil, almond oil, vegetable oil, and mixtures thereof. Triglycerides also encompass: tricaprylin, caprylic/capric triglyceride (e.g., Miglyol 801, Miglyol 812, Captex 355, and the like), caprylic/capric/linoleic triglyceride, caprylic/capric/succinic triglyceride, propylene glycol dicaprylate/dicaprate (e.g., Miglyol 840 and Captex 200, and the like), glycerol triacetate (triacetin), glyceryl stearates, and the like, including mixtures thereof. A preferred triglyceride is castor oil, glycerol triacetate, caprylic/capric/linoleic triglyceride, caprylic/capric/succinic triglyceride, propylene glycol dicaprylate/dicaprate (e.g., Miglyol 840 and Captex 200), caprylic/capric triglyceride, and mixtures thereof. A more preferred triglyceride is caprylic/capric triglyceride, glycerol triacetate, propylene glycol dicaprylate/dicaprate, castor oil, and mixtures thereof. An even more preferred triglyceride is caprylic/capric triglyceride. Another more preferred triglyceride is glycerol triacetate. Another more preferred triglyceride is propylene glycol dicaprylate/dicaprate. Another more preferred triglyceride is castor oil. When castor oil is the compositional triglyceride, then other glycerides and/or triglycerides, for example, propyl dicaprylates/dicaprates, caprylic/capric acid triglycerides or acylated monoglycerides, or mixtures thereof, are not required. An even more preferred caprylic/capric triglyceride is Miglyol 812. Another even more prefererred propylene glycol dicaprylate/dicaprate triglyceride is Miglyol 840.

In the present invention, the long-acting composition optionally comprises at least one preservative. In the present invention, the long-acting composition further comprises at least one preservative. The preservative can be an antimicrobial, antifungal, and/or antioxidant preservative. Non-limiting examples of preservatives include: benzoic acid, sorbic acid, ascorbic acid, citric acid, benzyl alcohol, tocopherols, ethanol, sodium bisulfate, chlorbutanol, 2-ethoxyethanol, methyl-, ethyl-, propyl, and butyl-parabens, and combinations thereof, chlorhexidine, phenol, butylated hydroxytoluene (BHT), butylated hydroxyanisole (BHA), sodium benzoate, mixtures thereof, and the like. A preferred preservative is selected from the group consisting of BHA, BHT, benzyl alcohol, and mixtures thereof.

In the present invention, the long-acting composition optionally comprises at least one additional veterinary acceptable excipient. In the present invention, the long-acting composition further comprises at least one additional veterinary acceptable excipient. For example, the additional veterinary excipient(s) can include buffering agents (e.g., sodium acetate, ammonium acetate, aspartic acid, diethanolamine, sodium carbonate, potassium phosphate, and the like), viscosity modifiers (e.g., aluminum stearates (mono- and di-stearates), sodium carboxymethylcellulose, methyl cellulose, and the like), solvents (e.g., benzyl benzoate, polyethylene glycol (e.g., PEG200, PEG 400, and the like), N,N-dimethylyacetamide, propylene glycol, ethanol, benzyl alcohol, dimethyl sulfoxide, N-methylpyrrolidone, 2-pyrrolidone, glycerol formal, glycerol, isopropyl myristate, tetraglycol (glycofurol, tetrahydrofurfuryl alcohol polyethylene glycol ether), diethylene glycol monoethyl ether (DEGMEE, e.g., transcutol), diethylene glycol monomethyl ether (DEGMME), and the like), emulsifier (e.g., polyethoxylated ethers, esters and oils such as macrogols, and phospholipids of which lecithin is an example, sorbitan esters (e.g., polysorbate 80 (Span 80), Span 40, Span 60, and the like)), cremophors (e.g., Cremaphor EL, Cremaphor RH40, and the like), polysorbates (e.g., Tween 20, Tween 80, and the like), polyethylene glycol-15-hydroxystearates (e.g., Kolliphor HS15, Crodasol HS15, and the like), macrogol 15 hydroxystearate, polyoxyethylene-polyoxypropylene copolymers and polyoxyethylene derivatives of vitamin E such as tocopheryl polyethylene glycol 1000 succinate, and the like), and a tonicity modifier (e.g., sorbitol, xylitol, mannitol, dextrose, glucose, propylene glycol, sucrose, inorganic salts such as sodium chloride and lactose, and the like).

Such compositions are prepared in a conventional manner in accordance with standard medicinal or veterinary practice.

The amounts of these ketoprofen ester prodrugs are easily determined by a skilled artisan and further depend on the dose amount and dose volume of the final long-acting composition. Said dose amounts and dose volumes are considered to be therapeutically effective dose amounts and dose volumes. Representative amounts of a therapeutically effective amount of a ketoprofen prodrug of Formula 1, Formula 2, or Formula 3, Formula 4, Formula 5, Formula 6, Formula 5 and Formula 6, and Formula 7, and mixtures thereof, ranges from about 0.1 to 20 mg/kg. More preferred representative amounts of the therapeutically effective amount of a ketoprofen ester prodrug ranges from about 0.25 to 15 mg/kg. Even more preferred representative amounts of a therapeutically effective amount of a ketoprofen ester prodrug ranges from about 0.5 to 12 mg/kg. Even more preferred representative amounts of a therapeutically effective amount of a ketoprofen ester prodrug ranges from about 0.5 to 10 mg/kg. Representative amounts of the ketoprofen ester prodrug in the composition ranges from about 1 mg/mL to about 500 mg/mL. A more preferred amount of the ketoprofen ester prodrug in the composition ranges from about 10 mg/mL to about 400 mg/mL. An even more preferred amount of the ketoprofen ester prodrug in the composition ranges from about 20 mg/mL to about 300 mg/m L.

The long-acting composition of the present invention is useful as an anti-inflammatory agent, anti-pyretic agent, and analgesic agent. The long-acting composition can be used in the fields of veterinary medicine, livestock husbandry and the maintenance of public health, i.e., to ensure the safety and health of food animals, particularly livestock, for example swine and cattle.

Systemic delivery of the ketoprofen prodrug via intramuscular injection or subcutaneous injection ensures that the entire treatment dose is delivered to the animal (i.e., cattle). The long-acting composition can be injected into the ear or at the junction of a pinna and the cranium of an animal. For example, the subcutaneous injection is administered at the junction of a pinna with the cranium using a sterile needle (e.g., 16 gauge, 1.5 to 2.0 cm) attached to a device such as a syringe, a repeating injector, a multi-dose syringe, and the like. The needle is directed caudal to the conchal eminence of the auricular cartilage, at the proximal end of the auricular cartilage near the base of the antiscaphal surface, and is directed rostrally from the caudal side of the ear. Preferably, injection is caudal to the cervicoauricularis muscles, and dorsocaudal to the parotid salivary gland. Once the needle is fully inserted, the drug administrator may draw back on a syringe plunger to assure that the needle is not in a blood vessel. Once in the subcutaneous tissue, an appropriate volume of the injectable long-acting composition is expelled through the needle, and the needle is subsequently withdrawn. Preferably, direct pressure is applied to the needle insertion point to minimize backflow of the injected composition. Even though the needle need not be inserted parallel to the skin, the method is still considered a subcutaneous injection because of the short needle length and the location of the injection site.

Needle injection is the preferred method of delivery, although use of syringes, automatic syringes, repeat-dose syringes, and injection guns can also be used in a similar manner.

Current treatment regimens, for example, Metacam® (meloxicam) is a once daily injectable for the control of pain and/or inflammation associated with arthritis. Subsequent doses should be administered 24-hours following the prior dose. Similarly, the recommended dose of flunixin meglumine injectable is once daily with repeat dosing up to 5 days for a horse. In cattle, the dose can be administered once a day as a single dose or divided into two doses administered once every 12 hours for up to 3-days. Ketoprofen (Anafen®) injectable is also administered by injection once daily for 1 (swine) to five (equine) days.

According to the present invention, the long-acting composition that comprises at least one of the ketoprofen ester prodrugs, at least one veterinary acceptable triglyceride, and optionally, at least one preservative, and optionally, at least one additional veterinary acceptable excipient can be used once every two, three, four, or five days, as needed. The long-acting composition provides for the treatment of pain, inflammation, and/or fever reduction for up to 48 hours, 72 hours, 96 hours, and in some instances for up to 120 hours following a single injectable dose. The long-acting composition, therefore, provides the animal with extended relief and likewise, reduces the number of injectable administrations by the animal caregiver.

According to the present invention, the long-acting composition that comprises at least one of the ketoprofen ester prodrugs, at least one veterinary acceptable triglyceride, and optionally, at least one preservative, and optionally, at least one additional veterinary acceptable excipient can further comprise an additional bioactive agent, for example an antibacterial agent. There are a variety of antibacterial agents available for use in animals. These antibacterial agents include, but are not limited to, the following: macrolides, for example, tulathromycin (Draxxin®), tildipirosin (Zuprevo®), tilmicosin (Micotil®), tylosin phosphate (Tylan®), and gamithromycin (Zactran®); cephalosporins, for example, ceftiofur sodium (e.g., Naxcel® and Excenel®), ceftiofur hydrochloride (e.g., Excenel RTU®, Excenel RTU EZ®, Spectramast®), ceftiofur crystalline free acid (Excede®), cefovecin sodium (Convenia®), and cefpodoxime proxetil (Simplicef®); lincosaminide antibiotics, for example, lincomycin (Lincomix), pirlimycin hydrochloride (Pirsue®), and clindamycin hydrochloride (Antirobe®); fluoroquinolones, for example, danofloxacin (Advocin®), enrofloxacin (Baytril®), and marbofloxacin (Zeniquin®); and tetracyclines, for example, chlortetracycline, oxytetracycline, and doxycycline. Other antibacterial agents include, but are not limited to, amoxicillin trihydrate and clavulonic acid (Clavamox®), spectinomycin (Adspec®), potentiated sulfonamides including trimethoprim/sulfadiazine (Tucoprim®) and sulfadimethoxine/ormetoprim (Primor®); and florfenicol (for example, Nuflor® and Nuflor® Gold).

In addition, the parent agent, ketoprofen, can also be combined with any one of the antibacterial agents disclosed herein, for example, ketoprofen and Draxxin®. The composition comprising both ketoprofen and Draxxin®, or ketoprofen and any other antibacterial agent described herein, may or may not be a composition that comprises a veterinary acceptable triglyceride and/or preservative, but can comprise at least one veterinary acceptable excipient, as described herein, and/or any additional veterinary acceptable excipient(s) known in the art for preparing a stable injectable composition for animals.

According to the present invention, the long-acting composition that comprises at least one ketoprofen ester prodrug, at least one veterinary acceptable triglyceride, and optionally, at least one preservative, and optionally, at least one additional veterinary acceptable excipient can be administered concomitantly or sequentially with an antibacterial agent, i.e., as two separate dosage units. Otherwise, the long-acting composition can further comprise an antibacterial agent that can be coadministered as a single injectable dosage unit. Similarly, ketoprofen can be concomitantly or sequentially administered with an antibacterial agent whether formulated together in a single injectable dosage unit or as separate dosage units.

Experimental

The esters of ketoprofen can be prepared in accordance with processes and methods as described herein. Alternatively, the methyl ester can be prepared according to the following scheme:

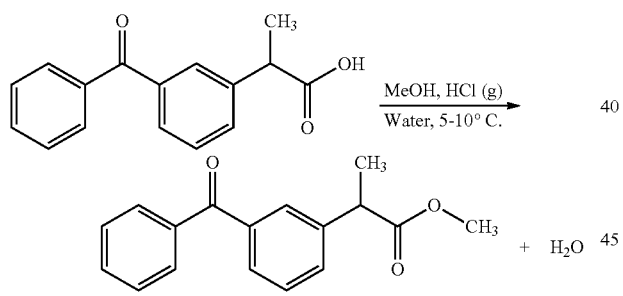

Ketoprofen (50 g) was added to methanol (200 mL) at room temperature and stirred until dissolved. The solution was cooled to about 5-10° C. HCl gas was passed through the solution to yield about a 23 g increase in reaction mass. The solution was warmed to room temperature while stirring. The solution was then cooled to about 0-5° C. Chilled water (200 mL) was added dropwise while maintaining a reaction temperature of about 0-20° C. The solution was then stirred at room temperature for about 30 minutes. The solids were filtered and washed with water. The solids were dried under vacuum at about 40° C. to yield about 52 g of ketoprofen methyl ester (98.6%).

EXAMPLES

In the following long-acting composition examples, the ketoprofen ester prodrug (KEP) can be any one of Formula 1 to Formula 7, and mixtures thereof. Non-limiting veterinary acceptable long-acting compositions are shown below.

Composition 1

| KEP | F1-F7, mixtures thereof | 30, 60, 80, 100, or 120 mg/mL |
|---|---|---|
| triglyceride | Miglyol 812 | q.s. 1 mL |
| preservative (optional) | BHA and/or BHT | 0.01-0.3% |

Composition 2

| KEP | F1-F7, mixtures thereof | 30, 60, 80, 100, or 120 mg/mL |
|---|---|---|
| triglyceride | Miglyol 812 | q.s. 1 mL |
| excipient | transcutol | 40-60% |
| preservative (optional) | BHA and/or BHT | 0.01-0.3% |

Composition 3

| KEP | F1-F7, mixtures thereof | 30, 60, 80, 100, or 120 mg/mL |
|---|---|---|
| triglyceride | Miglyol 812 | q.s. 1 mL |
| excipient | tetraglycol | 20-50% |
| preservative (optional) | BHA and/or BHT | 0.01-0.3% |

Composition 4

| KEP | F1-F7, mixtures thereof | 30, 60, 80, 100, or 120 mg/mL |
|---|---|---|
| triglyceride | Miglyol 812 | q.s. 1 mL |
| triglyceride | triacetin | 20-50% |
| preservative (optional) | BHA and/or BHT | 0.01-0.3% |

Composition 5

| KEP | F1-F7, mixtures thereof | 30, 60, 80, 100, or 120 mg/mL |
|---|---|---|
| triglyceride | Miglyol 812 | q.s. 1 mL |
| excipient | tetraglycol | 20-50% |
| excipient | Kolliphor HS15 | 3-10% |
| preservative (optional) | BHA and/or BHT | 0.01-0.3% |

Composition 6

| KEP | F1-F7, mixtures thereof | 30, 60, 80, 100, or 120 mg/mL |
|---|---|---|
| triglyceride | Miglyol 840 | q.s. 1 mL |
| preservative (optional) | BHA and/or BHT | 0.01-0.3% |

Composition 7

| KEP | F1-F7, mixtures thereof | 30, 60, 80, 100, or 120 mg/mL |
|---|---|---|
| triglyceride | Miglyol 840 | q.s. 1 mL |
| excipient | tetraglycol | 20-50% |
| preservative (optional) | BHA and/or BHT | 0.01-0.3% |

Composition 8

| KEP | F1-F7, mixtures thereof | 30, 60, 80, 100, or 120 mg/mL |
|---|---|---|
| triglyceride | Miglyol 840 | q.s. 1 mL |
| triglyceride | triacetin | 20-50% |
| preservative (optional) | BHA and/or BHT | 0.01-0.3% |

Composition 9

| KEP | F1-F7, mixtures thereof | 30, 60, 80, 100, or 120 mg/mL |
|---|---|---|
| triglyceride | Miglyol 840 | q.s. 1 mL |
| excipient | transcutol | 40-60% |
| preservative (optional) | BHA and/or BHT | 0.01-0.3% |

Composition 10

| KEP | F1-F7, mixtures thereof | 30, 60, 80, 100, or 120 mg/mL |
|---|---|---|
| triglyceride | Miglyol 840 | q.s. 1 mL |
| excipient | tetraglycol | 20-50% |
| excipient | Kolliphor HS15 | 3-10% |
| preservative (optional) | BHA and/or BHT | 0.01-0.3% |

Composition 11

| KEP | F1-F7, mixtures thereof | 30, 60, 80, 100, or 120 mg/mL |
|---|---|---|
| triglyceride | castor oil | q.s. 1 mL |
| preservative (optional) | BHA and/or BHT | 0.01-0.3% |

Composition 12

| KEP | F1-F7, mixtures thereof | 30, 60, 80, 100, or 120 mg/mL |
|---|---|---|
| triglyceride | castor oil | q.s. 1 mL |
| excipient | tetraglycol | 20-50% |
| preservative (optional) | BHA and/or BHT | 0.01-0.3% |

Composition 13

| KEP | F1-F7, mixtures thereof | 30, 60, 80, 100, or 120 mg/mL |
|---|---|---|
| triglyceride | castor oil | q.s. 1 mL |
| excipient | tetraglycol | 20-50% |
| excipient | Kolliphor HS15 | 3-10% |
| preservative (optional) | BHA and/or BHT | 0.01-0.3% |

Composition 14

| KEP | F1-F7, mixtures thereof | 30, 60, 80, 100, or 120 mg/mL |
|---|---|---|
| triglyceride | castor oil | q.s. 1 mL |
| excipient | transcutol | 40-60% |
| preservative (optional) | BHA and/or BHT | 0.01-0.3% |

Formula 1 (60 mg/mL or 120 mg/mL) in Composition 1 (without preservative) was shown to be stable in clear or amber glass vials or white HDPE vials at 25° C. and 40° C. and under accelerated stability conditions at 60% and 75% relative humidity. Addition of a preservative (e.g., benzyl alcohol or butylhydroxytoluene (BHT) provided similar stability results. Additionally, the 60 mg/mL composition was also stable at 4° C., 25° C., 40° C., 50° C., and 60° C., regardless of whether the vial head-space was filled with air or nitrogen.

BIOLOGICAL

The in vitro activity of numerous NSAIDs was evaluated against the swine COX-1 and COX-2 enzymes using a qualified primary cell assay using porcine alveolar macrophages. The NSAIDS included: flunixin meglumine (Banamine-S®), meloxicam (Metacam®), ketoprofen (Ketofen®, injectable), ketoprofen S-enantiomer, ketoprofen (racemic), carprofen, and ketoprofen prodrugs (Formula 1 and Formula 3). Alveolar macrophages were treated with a lipopolysaccharide (LPS), in the presence of varying amounts of inhibitors, to produce thromboxane B2 (TXB2) and/or prostaglandin $E_2$ ($PGE_2$). The cell supernatants were collected after 21-24 hours incubation and frozen at −80° C. until quantified by ELISA. TXB2 was used as the assay read-out for COX-1 inhibition. $PGE_2$ was used as the assay read-out for COX-2 inhibition. Each drug was tested in three different experiments on three different days (at a minimum). Percent inhibition of COX-1 or COX-2 was calculated for each drug concentration based on the mean of the TXB2 or $PGE_2$ concentration observed, respectively. The mean % inhibition curves (% inhibition versus drug concentration) were analyzed by non-linear regression to yield individual $IC_{50}$ and $IC_{90}$ values which are listed in rank order of COX-2 $IC_{50}$ potency. Racemic ketoprofen's $IC_{50}$ values against the swine COX enzymes (Table 1) are similar to those reported for human. As indicated in Table 1, ketoprofen (racemate) is slightly more potent than flunixin and both are an order of magnitude more potent than the ketoprofen methyl ester, which is about 5-times more potent than the classic COX-2 benchmark, Meloxicam.

TABLE 1

Swine COX-1 and COX-2 $IC_{50}$ and $IC_{90}$
Potencies (μM) for Various NSAIDs
Porcine Alveolar Macrophage COX Inhibitor Assay

| | COX-2 | | COX-1 | |
|---|---|---|---|---|
| NSAID | $IC_{50}$ (μM) | $IC_{90}$ (μM) | $IC_{50}$ (μM) | $IC_{90}$ (μM) |
| Ketoprofen (S)-enantiomer | 0.001 | 0.04 | 0.002 | 0.06 |
| Ketoprofen (racemic) | 0.006 | 0.08 | 0.007 | 0.08 |
| Ketofen ® | 0.03 | 0.65 | 0.12 | 6.11 |
| Flunixin | 0.033 | 0.507 | 0.066 | 0.747 |
| Formula 1 | 0.13 | 0.84 | 0.26 | 1.68 |
| Formula 3 | 0.12 | 0.93 | 0.15 | 4.86 |
| Meloxicam | 0.56 | 8.998 | 1.02 | 49.3 |
| Carprofen | 3.174 | 39.01 | 5.055 | 58.4 |

The in vitro activity of ketoprofen and Formula 1 also was evaluated against the bovine COX-1 and COX-2 enzymes using a bovine whole blood assay. Briefly, heparinized blood was collected for both assays. The COX-1 assay involved treatment of the blood with protamine; to reverse the anticoagulation effects of heparin; thus, inducing clotting and production of Thromboxane B2 (TXB2). The COX-2 assay involved treatment of blood with LPS to produce $PGE_2$. Both assays included the presence of varying amounts of inhibitors, to inhibit the TXB2 or PGE$_2$. Ketoprofen (Ketofen® injectable) and the ketoprofen prodrug ester, Formula 1, were each tested in three different experiments on three different days (at a minimum). Percent inhibition was calculated from the raw data for each drug dose based on the mean of the TXB2 or PGE$_2$ concentrations. Then the mean % inhibition curves (% inhibition versus drug concentration) were analyzed via non-linear regression to yield individual IC$_{50}$ and IC$_{90}$ values. As indicated in Table 2, ketoprofen (racemate) is more potent than Formula 1 at inhibiting the bovine COX-1 enzyme but shows similar potency to Formula 1 at the COX-2 enzyme. As compared with the swine COX enzymes, both ketoprofen and Formula 1 show lower potency against bovine COX-1 and COX-2.

TABLE 2

Bovine COX-1 and COX-2 IC$_{50}$ and IC$_{90}$ Potencies (µM) for Ketoprofen (Ketofen ® injectable) and Formula 1 Bovine in vitro Whole Blood COX Inhibitor Assays

| NSAID | IC$_{50}$ µM | | IC$_{90}$ µM | |
|---|---|---|---|---|
| | COX-1 | COX-2 | COX-1 | COX-2 |
| Ketofen ® | 0.03 | 0.06 | 0.12 | 0.47 |
| Formula 1 | 0.5 | 0.29 | 3.1 | 2.29 |

The pharmacokinetics of ketoprofen in gilts (about 15 kg) was assessed in an aqueous composition following intravenous and intramuscular administration at 0.5 mg/kg. Ketoprofen showed low systemic clearance (1.49±0.50 mL/min/kg), low volume of distribution (0.199±0.027 L/kg), terminal half-life time of 2.29±0.87 hours, and high bioavailability (121±9%) following intramuscular administration. Based on the pharmacokinetic results, a preclinical fever model involving intra-tracheal administration of swine influenza virus (SIV) was used to evaluate anti-pyretic efficacy of immediate-release ketoprofen (racemic), and to establish pharmacokinetic-pharmacodynamic (PK-PD) relationships for fever reduction, in post-weaning gilts. Intra-tracheal administration of SIV (4 mL 7.0±0.5 log$^{10}$ TCID 50/4 mL) results in a gradual rise in fever in swine, peaking at about 24 hours post administration and waning by about 40 hours post-administration. Five groups of young gilts (N=10 per group), approximately 28 days old, received intra-tracheal administration of SIV followed by intramuscular (IM) administration of ketoprofen at various doses (0, 0.03, 0.1, 0.3, and 1 mg/kg). Ketoprofen (racemic) was administered 23 hours after SIV administration. Rectal temperature readings were taken immediately before SIV administration (t=0 hour), both 1 hour before (t=22 hours) and 1 hour after (t=24 hours) ketoprofen administration and also at t=6, 27, 29, 32, and 35 hours. Racemic ketoprofen dose-dependently reduced fever in the SIV-induced fever model, with even the lowest dose tested (0.03 mg/kg, IM) showing statistically significant separation from vehicle. Strong anti-pyretic activity was associated with plasma concentrations as low as 500 nM. The data indicate that racemic ketoprofen is a potent anti-pyretic agent in swine.

A LPS-induced swine synovitis model was used to evaluate analgesic efficacy of immediate-release ketoprofen, and establish PK-PD relationships for pain reduction (which might be different from those associated with fever reduction), in post-weaning gilts. Anesthetized animals received a 2 mL LPS injection into the stifle joint. Following sufficient anesthesia recovery time, animals were assessed for lameness by transferring it from its pen to an open area and allowing it to move about spontaneously. An observer assigned a visual analogue scale (VAS) score for clinical lameness. Potential lameness scores range from 0 cm (corresponding to no deviation from normal movement) to 10 cm (corresponding to the worst possible lameness). Observations were repeated for up to 5 hours post-synovitis induction at which time the lameness subsides and the animals return to normal ambulation. In validation studies, both flunixin meglumine (2.2 mg/kg, IM), a product often used off-label to treat pain in swine, and meloxicam (0.2 mg/kg, IM), a compound approved in Europe as an analgesic for swine were effective at reducing LPS-induced lameness.

The ability of immediate-release ketoprofen to reduce LPS-induced lameness was evaluated. Two separate studies were performed to determine and refine the dose-response function of ketoprofen in the model. Additionally, blood samples were taken for correlation of ketoprofen plasma concentrations with efficacy (i.e., PK-PD assessment). The two studies were identical in methodology. Each study consisted of 36 pigs (N=9/treatment group); synovitis was induced at t=$^-$1 hour and ketoprofen was administered at t=0 hour. The pigs were examined at t=1, 2, 3, and 4 hours and assigned a VAS clinical lameness score. In the first study, a broad range of ketoprofen dose levels (0.01, 0.1, 1.0 mg/kg, IM) were compared with vehicle. Ketoprofen at 0.1 and 1.0 mg/kg produced statistically significant reductions in lameness, as compared with vehicle, for up to 3 hours post-dosing. Plasma concentrations determined that these doses produced total plasma concentrations around the in vitro IC$_{90}$ for both COX enzymes. A second, follow-on, study was performed to refine the dose-response curve by examining ketoprofen at dose levels of 0.01, 0.03 and 0.1 mg/kg, IM, as compared with vehicle. This study again demonstrated that 0.1 mg/kg ketoprofen produced maximal reductions in lameness for 3 hours post-dosing. This dose level corresponded to plasma concentrations between 0.5 and 0.7 µM of ketoprofen. In addition, bioavailability of ketoprofen was determined to be 100% following an IM injection.

The in-vitro and in-vivo results described above demonstrate that ketoprofen 1) is a potent inhibitor of swine COX isozymes, 2) has favorable pharmacokinetic properties in swine, and 3) is highly efficacious against both fever and pain in swine at total plasma concentrations as low as 500 nM. Ketoprofen is considered a hydrophilic agent that is not generally amenable to triglyceride-based compositions. Therefore, a triglyceride-based composition was contemplated with a ketoprofen ester prodrug which has lower aqueous solubility.

Ketoprofen prodrugs, Formula 1, Formula 2, and Formula 3, were evaluated in hydrolysis in swine plasma and liver microsomes. All Formula's (1-3) tested were hydrolyzed rapidly in swine liver microsomes and moderately or slowly in swine plasma. Hydrolyses of these ketoprofen esters were evaluated in vivo following single intravenous and intramuscular administration in swine at 0.5 mg/kg. Swine were dosed at 0.5 mg/kg of ketoprofen or its esters (Formula 1-3) either by intravenous (IV) or intramuscular injection. Plasma samples were assessed for ketoprofen and AUC's (nmol*hr/mL/µmol/kg) were normalized with dose of µmol/kg (n=3 or 4) are presented in Table 3.

TABLE 3

Normalized Average Ketoprofen AUCs in Swine Following Intravenous and Intramuscular Administration of Ketoprofen or its Esters

| Compound | AUC (IV) | AUC (IM) |
|---|---|---|
| Ketoprofen | 12.3 | 14.8 |
| Formula 1 | 14.6 | 12.4 |
| Formula 2 | 7.9 | 12.8 |
| Formula 3 | 9.3 | 4.9 |

As can be seen in Table 3, the ketoprofen exposure following administration of its methyl ester (Formula 1) is equivalent to the exposure following administration of ketoprofen itself.

As a result of the normalized exposure results, four long-acting compositions comprising Formula 1 were designed to assess ketoprofen pharmacokinetics. The compositions included co-solvents that would slowly dissipate from the injection site and/or intramuscular space over a duration of about 1-day to about 1-week and included: T01 (glycerol formal:triacetin (25:75 v/v)); T02 (miglyol 812); T03 (cottonseed oil:triacetin (90:10 v/v)); and T04 (a self micro-emulsifying drug delivery system) that potentially provides at least two advantages: 1) confers solution-like kinetics on a relatively hydrophobic compound, and/or 2) prolongs the length of time the active agent remains in solution and minimizes precipitation at the injection site, due to the presence of a significant level of emulsifying agents with a triglyceride. Gilts (n=4), female swine that have not been pregnant, weighing about 15 kg each received a single 3 mg/kg (30 mg/mL) intramuscular injection. As can be seen in Table 4, the miglyol 812 composition gave the lowest Cmax and the highest ketoprofen plasma concentration at 72 hours ($C72_{hrs}$). The $C24_{hr}$, $C48_{hr}$, and $C72_{hr}$ value is the ketoprofen plasma concentration at 24, 48, and 72 hours postdose, respectively.

TABLE 4

Average Pharmacokinetic Parameters of Ketoprofen in Swine Following a Single Intramuscular Administration of Ketoprofen Methyl Ester

| | AUC (0-72$_{hr}$) (µM · hr) | AUC (0-∞) (µM · hr) | Cmax (µM) | Tmax (hr) | t½ (hr) | C24$_{hr}$ (µM) | C48$_{hr}$ (µM) | C72$_{hr}$ (µM) |
|---|---|---|---|---|---|---|---|---|
| T01 | 99.9 | 99.9 | 4.77 | 5.0 | 7.92 | 1.36 | 0.20 | 0.04 |
| T02 | 68.8 | 81.4 | 2.51 | 4.5 | 58.1 | 0.85 | 0.37 | 0.30 |
| T03 | 106 | 108 | 3.68 | 6.0 | 18.8 | 1.70 | 0.44 | 0.19 |
| T04 | 145 | 145 | 15.4 | 2.5 | 6.45 | 0.31 | 0.02 | 0.01 |

A second composition study was conducted to assess Formula 1 (30 mg/mL or 60 mg/mL) compositions with additional components. For example, aluminum monostearate was added to the miglyol 812 composition to increase viscosity thereby decreasing the area for drug flux from the intramuscular space. Similarly, a surfactant (Span 80, 0.5% or 1%) was added to the miglyol 812 to decrease lag time for onset of triglyceride depletion, and castor oil which may provide different partitioning coefficients between the triglyceride and ester. The compositions included: T01 (miglyol 812, 30 mg/mL), T02 (miglyol 812 with aluminum monostearate, 30 mg/mL), T03 (miglyol 812, 60 mg/mL), T04 (miglyol 812 with 0.5% Span 80, 30 mg/mL), T05 (miglyol 812 with 1% Span 80, 30 mg/mL), and T06 (castor oil, 30 mg/mL). As can be seen in Table 5, increasing the ketoprofen methyl ester dose had no impact on the pharmacokinetic profile of ketoprofen. The addition of the viscosity modifier and/or the surfactants had no apparent effect on ketoprofen Cmax or duration. Further, the castor oil performed similarly to miglyol 812.

TABLE 5

Average Pharmacokinetic Parameters of Ketoprofen in Swine Following a Single Intramuscular Administration of Ketoprofen Methyl Ester

| | AUC (0-72$_{hr}$) (µM · hr) | AUC (0-∞) (µM · hr) | Cmax (µM) | Tmax (hr) | t½ (hr) | C24$_{hr}$ (µM) | C48$_{hr}$ (µM) | C72$_{hr}$ (µM) |
|---|---|---|---|---|---|---|---|---|
| T01 | 83.5 | 90.3 | 2.73 | 7.0 | 38.3 | 1.20 | 0.45 | 0.26 |
| T02 | 84.3 | 84.7 | 3.36 | 7.0 | 18.0 | 1.38 | 0.33 | 0.11 |
| T03 | 114 | 121 | 4.24 | 7.0 | 39.2 | 1.73 | 0.49 | 0.28 |
| T04 | 96.6 | 99.2 | 3.66 | 7.0 | 26.5 | 1.52 | 0.44 | 0.19 |
| T05 | 104 | 106 | 4.12 | 7.0 | 24.4 | 1.51 | 0.46 | 0.20 |
| T06 | 78.0 | 82.3 | 2.33 | 6.0 | 29.2 | 1.14 | 0.50 | 0.28 |

Additional pharmacokinetic studies were assessed in swine for Formula 1 in different injectable long term compositions. Compositions include: Composition 1: miglyol 812; Composition 3: migylol 812:tetraglycol (67:33, v/v); Composition 4: migylol 812:triacetin (75:25, v/v); Composition 5: miglyol 812:tetraglycol:Kolliphor HS15 (67:28:5, v/v/v). These compositions did not include the optional preservative. Table 6 shows the average pharmacokinetic values following a single 1 mg/kg intramuscular injection for each of the compositions comprising 80 mg/mL of Formula 1 in sows (n=4), each weighing between 184 to 233 kg.

TABLE 6

Average Pharmacokinetic Parameters of Ketoprofen in Swine Following a Single Intramuscular Administration of Ketoprofen Methyl Ester

| | AUC (0-72$_{hr}$) (µM · hr) | AUC (0-∞) (µM · hr) | Cmax (µM) | Tmax (hr) | t½ (hr) | C24$_{hr}$ (µM) | C48$_{hr}$ (µM) | C72$_{hr}$ (µM) |
|---|---|---|---|---|---|---|---|---|
| 1 | 67.6 | 82.7 | 1.64 | 7.0 | 54.5 | 1.17 | 0.43 | 0.23 |
| 3 | 72.1 | 82.4 | 2.03 | 7.0 | 40.1 | 1.10 | 0.42 | 0.25 |
| 4 | 73.7 | 80.2 | 2.22 | 10.0 | 34.8 | 1.32 | 0.37 | 0.19 |
| 5 | 57.5 | 75.2 | 1.23 | 6.0 | 60.3 | 0.81 | 0.42 | 0.27 |

Additional pharmacokinetic studies were assessed in swine for Formula 1 in different injectable long term compositions. Compositions include: Composition 6: Migylol 840; Composition 7: Migylol 840:tetraglycol (67:33); Composition 8: Migylol 840:triacetin (75:25); and Composition 10: Migylol 840:tetraglycol:Kolliphor HS15 (67:28:5). These compositions did not include the optional preservative. Table 7 shows the average pharmacokinetic values following a single 1 mg/kg intramuscular injection for each of the compositions comprising 80 mg/mL of Formula 1 in sows (n=4) weighing between 184 to 233 kg.

TABLE 7

Average Pharmacokinetic Parameters of Ketoprofen in Swine Following a Single Intramuscular Administration of Ketoprofen Methyl Ester

| | AUC (0-72$_{hr}$) (µM · hr) | AUC (0-∞) (µM · hr) | Cmax (µM) | Tmax (hr) | t½ (hr) | C24$_{hr}$ (µM) | C48$_{hr}$ (µM) | C72$_{hr}$ (µM) |
|---|---|---|---|---|---|---|---|---|
| 6 | 69.1 | 70.7 | 1.89 | 7.0 | 21.9 | 1.29 | 0.47 | 0.19 |
| 7 | 69.6 | 79.0 | 1.79 | 7.0 | 38.5 | 1.17 | 0.47 | 0.26 |

TABLE 7-continued

Average Pharmacokinetic Parameters of Ketoprofen in Swine Following a Single Intramuscular Administration of Ketoprofen Methyl Ester

| | AUC (0-72$_{hr}$) (µM · hr) | AUC (0-∞) (µM · hr) | Cmax (µM) | Tmax (hr) | t½ (hr) | C24$_{hr}$ (µM) | C48$_{hr}$ (µM) | C72$_{hr}$ (µM) |
|---|---|---|---|---|---|---|---|---|
| 8 | 66.4 | 67.8 | 1.89 | 7.0 | 21.7 | 1.17 | 0.41 | 0.19 |
| 10 | 49.7 | 73.1 | 1.05 | 7.0 | 78.3 | 0.80 | 0.33 | 0.20 |

In an effort to evaluate the magnitude and duration of efficacy of Formula 1 in Miglyol 812 (30 mg/mL) against fever in swine (particularly gilts), animals were given a 6 mg/kg dose by intramuscular injection, except where specifically described. Based on earlier PK-PD studies with immediate-release ketoprofen in the swine SIV-induced fever model, the 6 mg/kg dose was predicted to confer total plasma concentrations of ketoprofen of ≥500 nM for 72 hours. Four treatment groups were compared with vehicle and included: T01 (immediate release ketoprofen (1 mg/kg, IM, administered 1 hour prior to peak fever), T02 (Formula 1, administered 24 hours prior to SIV challenge (i.e., peak fever), T03 (Formula 1, administered 48 hours prior to SIV challenge), and T04 (Formula 1, administered 72 hours prior to SIV challenge). In all cases, rectal temperatures were measured at 6, 20, 23, 24, 26, 28, 31, and 34 hours post SIV challenge. Data is presented in FIG. 1. Data are plotted as least square means±SEMs with error bars representing the standard error of the mean (SEM). Mean plasma concentrations of ketoprofen determined at 24, 48 and 72 hours post-dose (satellite PK group) are shown: FIG. 1A: ketoprofen (immediate-release) dosed 23 hours after SIV challenge; FIG. 1B: ketoprofen methyl ester in Miglyol 812 (6 mg/kg, IM) dosed at the same time as SIV challenge (i.e., 24 hours prior to peak fever); FIG. 1C: ketoprofen methyl ester in Miglyol 812 (6 mg/kg, IM) dosed 24 hours before SIV challenge (i.e., 48 hours prior to peak fever); FIG. 1D: ketoprofen methyl ester in Miglyol 812 (6 mg/kg, IM) dosed 48 hours before SIV challenge (i.e., 72 hours prior to peak fever). In FIG. 1, the "*" designates points of statistical significance (P<0.05) as compared with vehicle. N=10/group.

As can be seen from FIGS. 1B, 1C, and 1D, administration Formula 1 in Miglyol 812 resulted in statistically significant reductions in rectal temperature at timepoints 10-79 hours post-dose. A satellite PK group run in parallel with the efficacy study showed that mean plasma concentrations associated with the composition were 3.67, 1.19 and 0.52 µM at 24, 48 and 72 hours post-dose, respectively; this was consistent with the prediction that 6 mg/kg would maintain plasma concentrations above ≥500 nM for 72 hours.

In order to evaluate onset of antipyretic efficacy, Formula 1 in Miglyol 812 was evaluated in the early hours post-dose in the SIV fever model. Five groups of young gilts (N=10 per group) received intra-tracheal administration of SIV followed by intramuscular administration of Formula 1 compound at various doses (0, 4, 5, 6 mg/kg) or Banamine (2.2 mg/kg, IM) as a positive control. All dose groups were administered test agent 24 hours after SIV administration. Rectal temperature readings were taken immediately before SIV administration (t=0 hour), both 3 hours before (t=21 hours) and 1 hour after (t=25 hours) dose administration and also at t=7, 27, 29, 32, and 35 hours (effects of ketoprofen methyl ester in Miglyol 812 (4, 5, 6 mg/kg, IM), as compared with vehicle, in the initial hours post-dose). Results are shown in FIG. 2. Data are plotted as least square means±SEMs, with error bars also representing SEM. Time course of plasma concentrations associated with the different dose levels evaluated at 0.5, 1 and 3 hours post-dose (satellite PK group).

As can be seen in FIG. 2, all Formula 1 doses significantly reduced fever, as compared with vehicle, starting 1 hour post-dose and continuing for all timepoints examined. Importantly, all dose groups remained active, as compared with vehicle, at t=35 hours (i.e., 11 hours post-dose), while Banamine did not. Consistent with the PK profile associated with the Miglyol 812 composition, the satellite PK group showed that exposure levels for all doses were well above the COX-1 and COX-2 in vitro IC$_{90}$ values at 0.5, 1 and 3 hours post-dose. In conclusion, the anti-pyretic effects of the Miglyol 812 composition in young gilts can be summarized as follows: 1) Formula 1 dosed at 4, 5 and 6 mg/kg, IM shows anti-pyretic efficacy starting 1 hour post-dose; 2) 6 mg/kg, IM continues to show anti-pyretic activity through 72 hours post-dose, but decreasing doses show a corresponding decrease in the duration of anti-pyretic efficacy. In FIG. 2, the "*" designates points of statistical significance (P<0.05) as compared with vehicle. N=10/group.

The onset and duration of the ketoprofen methyl ester in Miglyol 812 (6.0 mg/kg, IM) was tested in a swine synovitis model. For this particular study, each gilt underwent two synovitis inductions—once on Day 0 and again on Day 3. On Day 0, t=−1 hour, synovitis was induced by injecting LPS into the right stifle, followed by dosing of either the Formula 1-Miglyol 812 composition (N=9) or vehicle (N=9) at t=0 hour. Lameness assessment corresponded to hours 1-4 post dose administration. On Day 3, synovitis was induced again in each gilt by injecting a LPS into the left stifle (i.e., at t=71 hours). Lameness assessments on Day 3 corresponded to 73-76 hour post dose administration. Results are shown in FIG. 3. Data are expressed as least squares means with 90% confidence limits (N=9/group). *P<0.05, as compared with vehicle. The error bars for graph "A" of FIG. 3 depict 95% confidence limits and the error bars on graph "B" of FIG. 3 are SEM. Ketoprofen methyl ester in Miglyol 812 (6 mg/kg, IM) produced a significant reduction in lameness within 1 hour of administration on Day 0. On Day 3, lameness still was significantly reduced compared to placebo out to 74 hours post-dose (FIG. 3A). Additionally, plasma levels confirmed that the in vitro IC$_{90}$ of both COX enzymes was covered for the duration of this study (FIG. 3B).

Ketoprofen plasma pharmacokinetics following an intramuscular dose of ketoprofen methyl ester was also evaluated in intact male cattle. Compositions included: Composition 1: 120 mg/mL of ketoprofen methyl ester in miglyol 812 without preservative; Composition 2: 160 mg/mL of ketoprofen methyl ester in miglyol 812:transcutol (50:50, v/v); and Composition 4: 160 mg/mL of ketoprofen methyl ester in miglyol 812:triacetin (80:20, v/v). For compositions 1 and 2, three heifers (220-300 kg) each received a 6 mg/kg intramuscular dose and for composition 4, two heifers (180-240 kg) each received a 6 mg/kg intramuscular dose. Following a single intramuscular injection of ketoprofen methyl ester, the average plasma concentration of ketoprofen remained higher than ketoprofen's in vitro IC$_{90}$ for inhibition of the bovine COX-1 enzyme for 120 hours and remained higher than ketoprofen's in vitro IC$_{90}$ for inhibition of the bovine COX-2 enzyme for almost 72 hours. Results are shown in Table 8.

TABLE 8

Average Pharmacokinetic Parameters of Ketoprofen in Cattle Following a Single Intramuscular Administration of Ketoprofen Methyl Ester

| | AUC (0-72$_{hr}$) (µM · hr) | AUC (0-∞) (µM · hr) | Cmax (µM) | Tmax (hr) | t½ (hr) | C24$_{hr}$ (µM) | C48$_{hr}$ (µM) | C72$_{hr}$ (µM) |
|---|---|---|---|---|---|---|---|---|
| 1 | 88.8 | 106 | 1.67 | 7.0 | 48.4 | 1.23 | 0.75 | 0.47 |
| 2 | 104 | 123 | 2.38 | 7.0 | 48.8 | 2.13 | 0.66 | 0.44 |
| 4 | 115 | 126 | 2.65 | 2.7 | 32.4 | 2.13 | 0.66 | 0.44 |

The data in Table 8 indicate that when ketoprofen methyl ester in Miglyol 812 is dosed once by intramuscular injection to cattle, the composition confers similar extended-release properties as those observed in swine, resulting in prolonged plasma exposure of ketoprofen at levels sufficient to inhibit the bovine COX enzymes for 3-5 days.

As a comparison, the average ketoprofen pharmacokinetics of a non-sustained injectable composition of ketoprofen (3 mg/kg; Neoprofen®, 100 mg/mL)) given to cattle (calves, between 6-12 months of age) with an average body weight of about 91 kg is presented in Table 9. Singh, R., et. al., Wayamba Journal of Animal Science, 6, 2014, pg. 820-823.

TABLE 9

Average Pharmacokinetic Parameters of Ketoprofen Following a Single Intramuscular Injection of Neoprofen®

| AUC (µM*hr) | Cmax (µM) | Tmax (hr) | T½ (hr) |
|---|---|---|---|
| 69.7 | 24.2 | 0.5 | 3.40 |

As can be observed between Tables 8 and 9, the ketoprofen t½ following the methyl ester prodrug (Formula 1) is approximately 14 times (compositions 1 and 2) longer and approximately 9.5 times longer (composition 4) in cattle when compared to the commercial injectable product Neoprofen®. As such, the longer T½ will correlate with extended therapeutic plasma concentrations and hence longer duration of efficacy following a single injectable dose.

We claim:

1. An injectable veterinary long-acting composition comprising
   a) a ketoprofen methyl ester prodrug in the amount of about 20-300 mg/mL; b) a veterinary acceptable triglyceride that is a caprylic/capric acid triglyceride;
   c) at least one preservative, and
   d) a veterinary acceptable excipient that is a solvent selected from the group consisting of benzyl benzoate, polyethylene glycol, N,N-dimethylyacetamide, propylene glycol, ethanol, benzyl alcohol, dimethyl sulfoxide, N-methylpyrrolidone, 2-pyrrolidone, glycerol formal, glycerol, isopropyl myristate, tetraglycol, diethylene glycol monoethyl ether and diethylene glycol monomethyl ether; and wherein said composition provides for the treatment of pain, inflammation, and/or fever reduction for up to 120 hours following a single injectable dose.

2. The veterinary long-acting composition of claim 1 wherein the veterinary acceptable solvent is benzyl benzoate.

3. The veterinary long-acting composition of claim 2 wherein the veterinary acceptable caprylic/capric triglyceride is Miglyol 812.

4. The veterinary long-acting composition of claim 1 wherein the at least one preservative is benzyl alcohol.

* * * * *